United States Patent [19]

Lee

[11] Patent Number: 4,999,290
[45] Date of Patent: Mar. 12, 1991

[54] DETECTION OF GENOMIC ABNORMALITIES WITH UNIQUE ABERRANT GENE TRANSCRIPTS

[75] Inventor: Ming-Sheng Lee, Houston, Tex.

[73] Assignee: The Board of Regents, The University of Texas System, Austin, Tex.

[21] Appl. No.: 175,833

[22] Filed: Mar. 31, 1988

[51] Int. Cl.$^5$ .................. C12Q 1/68; C07H 15/12; C12N 15/00
[52] U.S. Cl. .......................... 435/6; 536/27; 935/21; 935/77; 935/78
[58] Field of Search ............. 435/6; 536/27; 935/21, 935/77, 78

[56] References Cited

U.S. PATENT DOCUMENTS

| | | | |
|---|---|---|---|
| 4,358,586 | 11/1982 | Rubin | 536/27 |
| 4,683,202 | 7/1987 | Mullis | 435/91 |

FOREIGN PATENT DOCUMENTS

| | | | |
|---|---|---|---|
| 0209702 | 1/1987 | European Pat. Off. | 435/6 |
| 0260032 | 3/1988 | European Pat. Off. | 536/27 |

OTHER PUBLICATIONS

International Search Report, PCT/US89/01218, 22 Mar., 1989.
Blood, vol. 72, No. 3, 9/88, Grune & Stratton, Inc., M. S. Lee et al., "Detection of Minimal Residual bcr/abl Transcripts by a Modified Polymerase Chain Reaction", pp. 893–896.
Chem. Abstr., vol. 107, No. 5, 8/3/87, Columbus, OH, US; E. Shtivelman et al., "The bcr–abl RNA in Patients with Chronic Myelogenous Leukemia", p. 490, Abstract #37417v & Blood, 1987, 69(3), 971–973.
Chem. Abstr., vol. 105, No. 25, 12/22/86; Columbus, OH, US, S.A. Quarles et al., "The Use of Complementary RNA and S1 Nuclease for the Detection and Quantitation of Low Abundance mRNA Transcripts", P. 396, Abstr. No. 222148e & BioTechniques, 1986, 4(5), 434–438.
Hu et al., Detection of B–Cell Lymphoma in Peripheral Blood by DNA Hybridisation, The Lancet, Nov. 16, 1985, pp. 1092–1095.

(List continued on next page.)

Primary Examiner—Robert A. Wax
Assistant Examiner—M. Fleisher
Attorney, Agent, or Firm—Arnold, White & Durkee

[57] ABSTRACT

The present invention involves a method for detecting the unique aberrant gene transcripts of a targeted cellular genomic abnormality in a tissue sample. This method comprises a series of steps. Initially, total cellular RNA or m-RNA is preferred from the tissue sample to be analyzed for the presence of a genomic abnormality. The total cellular RNA or m-RNA is then mixed with at least one synthetic DNA oligonucleotide complementary to the unique RNA sequence of the targeted cellular genomic abnormality being detected. The mixing is under conditions facilitating formation of double stranded DNA-RNA heteroduplexes when a strand of synthetic DNA oligonucleotide is complementary to an RNA strand obtained from the tissue sample. The conditions are those such as time, salt concentration, temperature and pH 10. The synthetic DNA oligonucleotide is preferably about several hundred nucleotides in length, more preferably about 60 to about 150 nucleotides in length.

In a most preferred embodiment, the method of the present invention may be applied to the detection of residual cells of chronic myelogenous leukemia with its characteristic Philadelphia chromosome (Ph$^1$). For this situation, the first primer is primer bcr Ex III(+) or bcr Ex II (+), most preferably a mixture of primer bcr Ex III (+) and bcr Ex II (+). In certain instances the second primer may also be a mixture of two different primers, particularly where there is a variable breakpoint in the second chromosomal member of the translocation characteristic of a neoplasm. Where residual cells of chronic myelogenous leukemia are being detected, the second primer is most preferably primer abl (−).

27 Claims, 4 Drawing Sheets

OTHER PUBLICATIONS

Cleary et al., Immunoglobulin Gene Rearrangement as a Diagnostic Criterion of B-cell Lymphoma, Proc. Natl. Acad. Sci. USA vol. 81, pp. 593-597.

Saiki et al., Enzymatic Amplification of B-Globin Genomic Sequences and Restriction Site Analysis for Diagnosis of Sickle Cell Anemia, Science, vol. 230, Dec. 1985, pp. 1350-1354.

Lee et al., Detection of Minimal Residual Cells Carrying the t(14;18) by DNA Sequence Amplification, Science vol. 237, Jul. 1987.

Saiki et al., Primer-Directed Enzymatic Amplification of DNA with a Thermostable DNA Polymerase, Science, vol. 239, Jan. 1988, pp. 487-491.

Stoflet et al., Genomic Amplification with Transcript Sequencing, Science, vol. 239, Jan. 1988, pp. 491-494.

Mullis et al., Specific Enzymatic Amplification of DNA in Vitro: The Polymerase Chain Reaction, Cold Spring Harbor Symposia on Quantitative Biology, vol. Li, 1986, pp. 263-273.

Scharf et al., Direct Cloning and Sequence Analysis of Enzymatically Amplified Genomic Sequences, Science, vol. 233, Sep. 1986, pp. 1076-1078.

Bialy et al., Amplified Genes and Frame-Shift Mutations, Bio/Technology, vol. 5, Dec. 1987, p. 1268.

Wrischnik et al., Length Mutations in Human Mitochondrial DNA: Direct Sequencing of Enzymatically Amplified DNA, Nucleic Acids Research, vol. 15, No. 2, 1987, pp. 529-543.

Rollo et al., Polymerase Chain Reaction Fingerprints, Nucleic Acids Research, vol. 15, No. 21, 1987, p. 9094.

Saiki et al., Analysis of Enzymatically Amplified B--globin and HLA-DQa DNA with Allele-Specific Oligonucleotide Probes, Nature, vol. 324, Nov. 13, 1986, pp. 163-166.

Lee et al., The Gene Located at Chromosome 18 Band q21 Is Rearranged in Uncultured Diffuse Lymphomas as Well as Follicular Lymphomas, Blood, vol. 70, No. 1, Jul. 1987, pp. 90-95.

Weiss et al., Molecular Analysis of the t(14;18) Chromosomal Translocation in Malignant Lymphomas, The New England Journal of Medicine, vol. 317, No. 19, Nove. 5, 1987, pp. 1185-1189.

Tsukimoto et al., The t(14;18) Chromosome Translocations Involved in B-Cell Neoplasms Result from Mistakes in VDJ Joining, Science, vol. 229, Sep. 1985, pp. 1390-1393.

Ravetch et al., Structure of the Human Immunoglobulin u Locus: Characterization of Embryonic and Rearranged J and D Genes, Cell, vol. 27, Dec. 1981, pp. 583-591.

Tsujimoto et al., Analysis of the Structure, Transcripts, and Protein Products of bel-2, The Gene Involved in Human Follicular Lymphoma, Proc. Natl. Acad. Sci. USA 83 (1986), pp. 5214-5218.

Cleary et al., Cloning and Structural Analysis of cDNAs for bcl-2 and a Hybrid bcl-2/Immunoglobulin Transcript Resulting from the t(14;18) Translocation, Cell, vol. 47, Oct. 10, 1986, pp. 19-28.

Bakhshi et al., Mechanism of the t(14;18) Chromosomal Translocation: Structural Analysis of Both Derivative 14 and 18 Reciprocal Partners, Proc. Natl. Acad. Sci. USA, vol. 84, Apr. 1987, pp. 2396-2400.

Whang-Peng et al., Clinical Implications of Cytogenetic Variants in Chronic Myelocytic Leukemia (CML), Blood, vol. 32, No. 5, Nov. 1968, pp. 755-766.

Groffen et al., Philadelphia Chromosomal Breakpoints are Clustered within a Limited Region, bcr, on Chromosome 22, Cell vol. 36, Jan. 1984, pp. 93-99.

Heisterkamp et al., Structural Organization of the bcr Gene and Its Role in the Ph' Translocation, Nature, vol. 315, Jun. 1985, pp. 758-761.

Heisterkamp et al., Localization of the C-abl Oncogene Adjacent to a Translocation Break Point in Chronic Myelocytic Leukaemia, Nature, vol. 306, Nov. 17, 1983, pp. 239-242.

Shtivelman et al., Alternative Splicing of RNAs Transcribed from the Human abl Gene and from the bcr-abl Fused Gene, Cell, vol. 47, Oct. 24, 1986, pp. 277-284.

Shtivelman et al., ber-abl RNA in Patients with Chronic Myelogenous Leukemia, Blood, vol. 69, Mar. 1987, pp. 971-973.

Berk et al., Sizing and Mapping of Early Adenovirus mRNAs by Gel Electrophoresis of S1 Endonuclease-Digested Hybrids, Cell, vol. 12, Nov. 1977, pp. 721-732.

Ando, A Nuclease Specific for Heat-Denatured DNA Isolated from a Product of Aspergillus Oryzae, Biochimica Et Biophysica Acta, 114, 1966, pp. 158-168.

(List continued on next page.)

OTHER PUBLICATIONS

Tsujimoto et al., Involvement of the bcl-2 Gene in Human Follicular Lymphoma, Science, vol. 228, Jun. 21, 1985, pp. 1440–1443.

Fukuhara et al., Chromosome Abnormalities in Poorly Differentiated Lymphocytic Lymphoma, Cancer Research, vol. 39, Aug. 1979, pp. 3119–3128.

Yunis et al., Distinctive Chromosomal Abnormalities in Histologic Subtypes of Non-Hodgkins's Lymphoma, The New England Journal of Medicine, vol. 307, No. 20, Nov. 11, 1982, pp. 1231–1236.

Bloomfield et al., Nonrandom Abnormalities in Lymphoma, Cancer Research, vol. 43, Jun. 1983, pp. 2975–2984.

Tsujimoto et al., Cloning of the Chromosome Breakpoint of Neoplastic B Cells with the t(14;18) Chromosome Translocation, Science, vol. 226, Nov. 30, 1984, pp. 1097–1099.

Bakshi et al., Cloning the Chromosomal Breakpoint of t(14;18) Human Lymphomas: Clustering around $J_H$ on Chromosome 14 and Near a Transcriptional Unit on 18, Cell, vol. 41, Jul. 1985, pp. 899–906.

Cleary et al., Nucleotide Sequence of a t(14;18) Chromosomal Breakpoint in Follicular Lumphoma and Demonstration of a Breakpoint-cluster Region Near a Transcriptionally Active Locus on Chromosome 18, Proc. Natl. Acad. Sci. USA, vol. 82, Nov. 1985, pp. 7439–7443.

Saiki et al., Enzymatic Amplification of B-Globin Genomic Sequences and Restriction Site Analysis for Diagnosis of Sickle Cell Anemia, Science, vol. 230, Dec. 20, 1985, pp. 1350–1354.

Smith et al., Ciculating Monoclonal B Lymphocytes in Non-Hodgkins's Lymphoma, The New Englas Journal of Medicine, vol. 311, No. 23, Dec. 6, 1984, pp. 1476–1481.

Imprain et al, Biochemical and Biophysical Research Communication, Feb. 13, 1987, vol. 142, No. 3, pp. 710–716.

PRIMER BCR EX (+)5'-GTCATCGTCCAC-3'

ANTI-K28 3'-AAAGACTTACAGTAGCAGGTGAGTCGGTGACCTAAATCGTCTCAAGTTTCGGGAAGTCGCCGGTCATCGTAGACTGAAACTCGGAGTCCAGACTCA-5'

PRIMER ABL(-) 3'-GAAACTCGGAGT-5'

PRIMER BCR EX (-)5'-CAGACTGTCCAC-3'

ANTI-L6 3'-CACTTTGAGGTCTGACAGGTGTCGTAAGGCGACTGGTAGTTATTCCTTCTTCGGGAAGTCGCCGGTCATCGTAGACTGAAACTCGGAGTCCAGACTCA-5'

PRIMER ABL(-) 3'-GAAACTCGGAGT-5'

|← 80 bp →|

B.

PRIMER 18q21 (+)5'-TTTGAGCTTTAG-3'

MSL-60 3'-AAACTGGAAATCGACGATCCAAGTTCTGAGTTCCAGGTTAGACTGTACAGAGGAGTCCA-5'

PRIMER JH(-) 3'-CAGAGGAGTCCA-5'

|← 60 bp →|

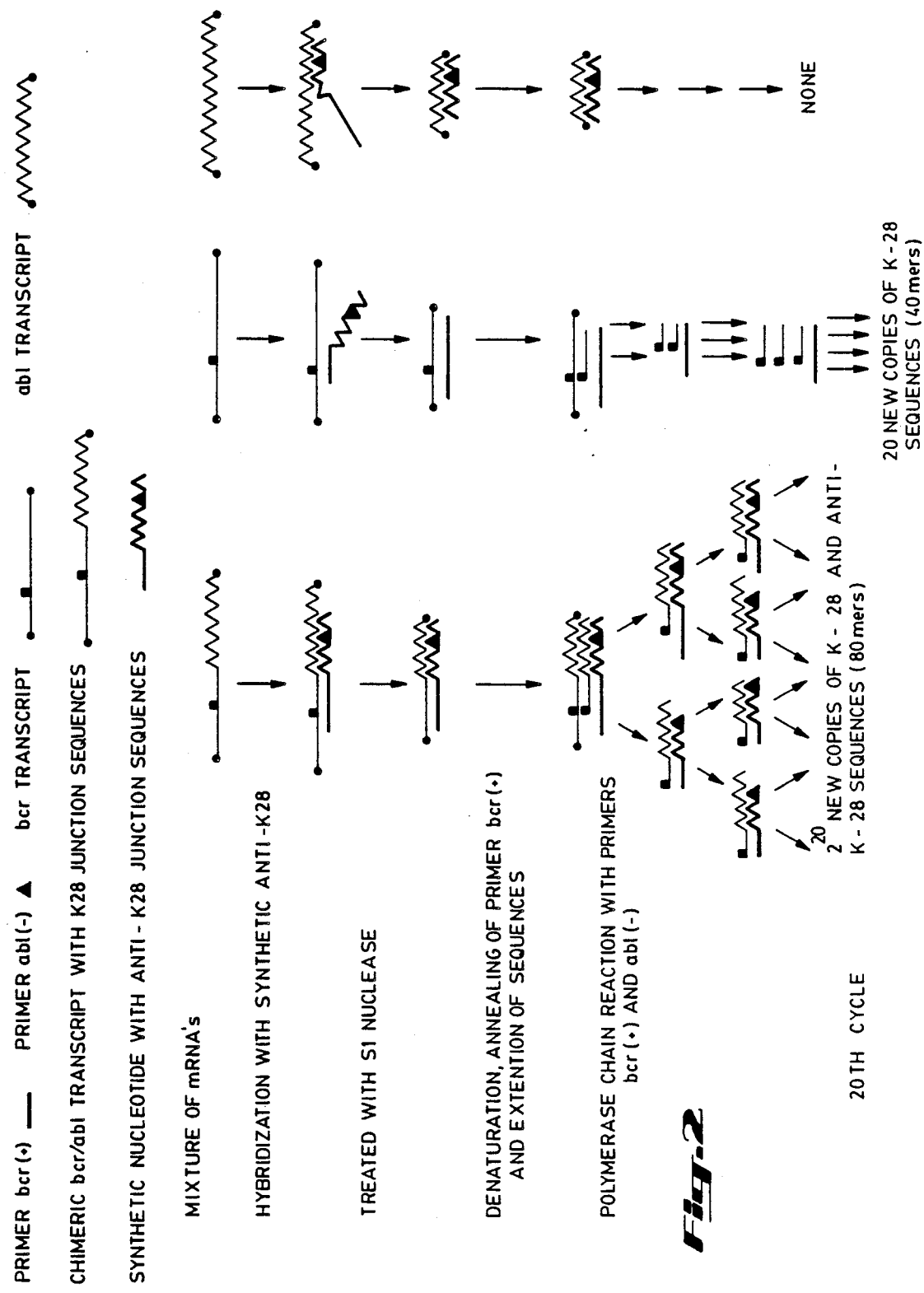

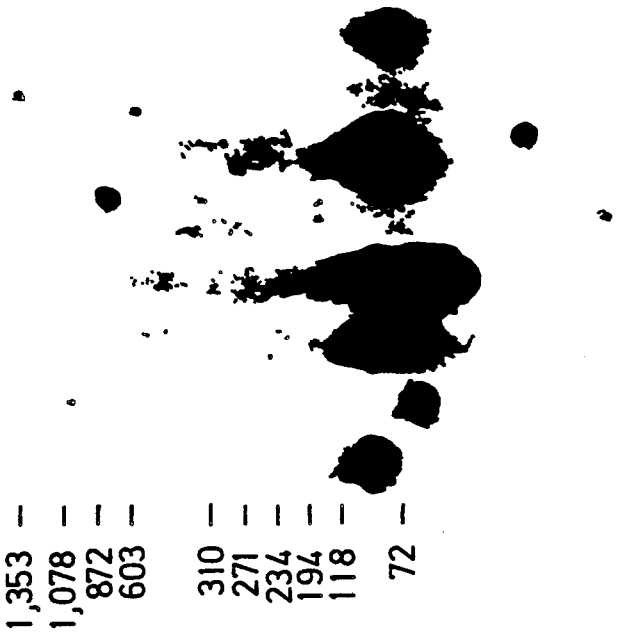
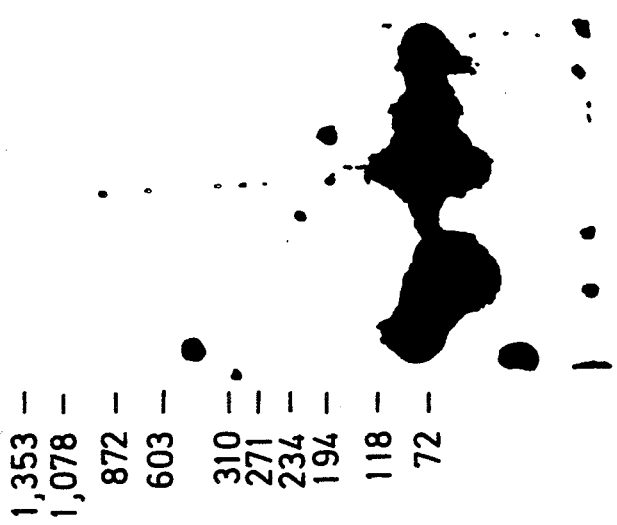

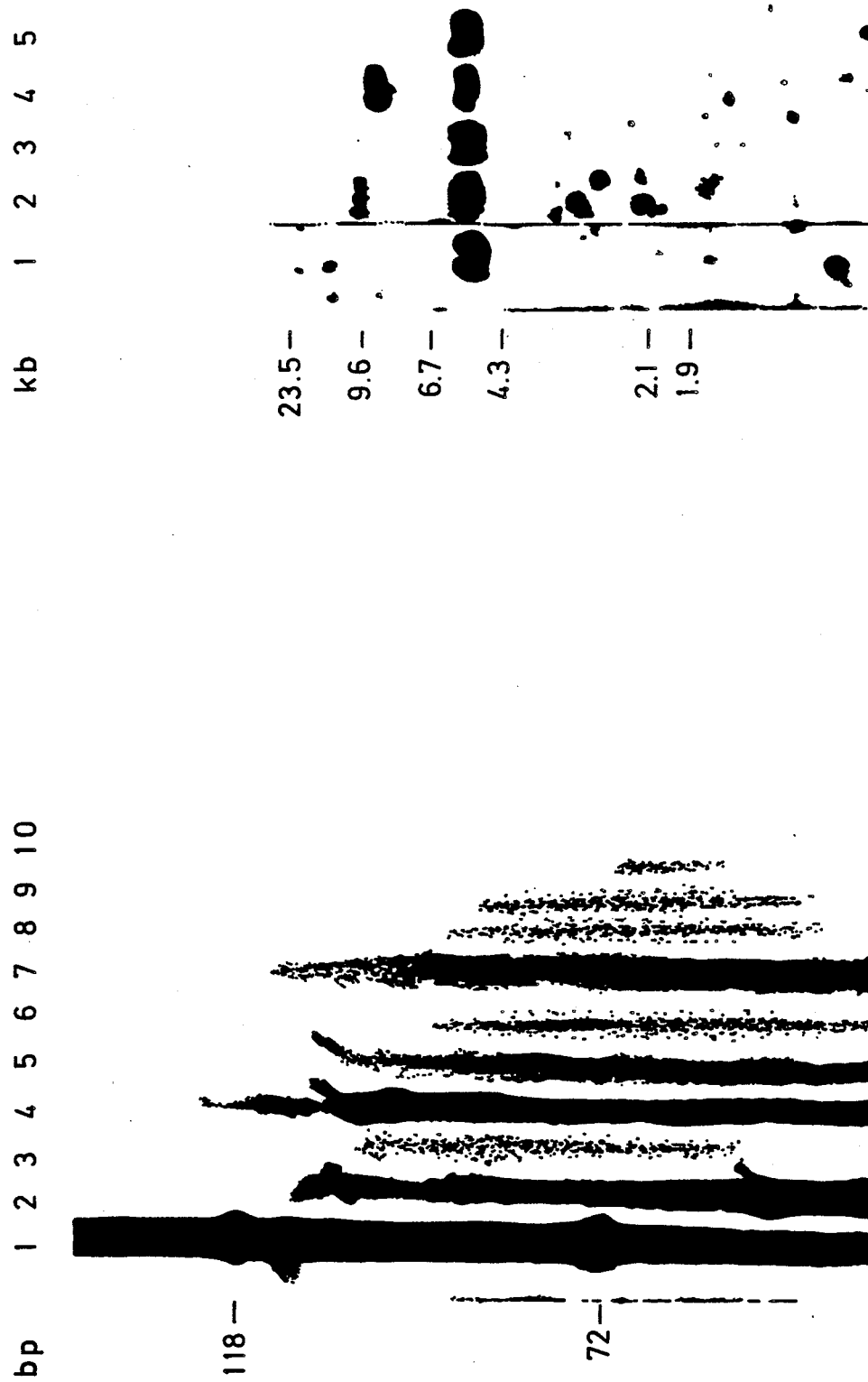

DETECTION OF GENOMIC ABNORMALITIES WITH UNIQUE ABERRANT GENE TRANSCRIPTS

BACKGROUND OF THE INVENTION

The present invention involves using a new technique for the detection of genomic abnormalities. Such detection may prove particularly useful to predict recurrence of cancer, or early detection of cancer.

High frequency of recurrence is one of the major problems in cancer treatment. Relapse from clinically undetectable residual disease is the most likely mechanism (1). Detection of minimal disease is extremely difficult since tumor specific markers are not readily available. Molecular technology has provided a means to demonstrate residual disease by identifying clonal gene rearrangement patterns that may present, for example, in malignant hematopoietic cells (2). Southern blot hybridization may detect neoplastic cells at levels as low as 1% of the total number of cells (3). However, one of the major drawbacks in using such traditional methods is that it is difficult to be certain that faint nongermline bands indeed represent clonal rearrangements representative of neoplastic cells. Furthermore, no rearranged bands can usually be detected by traditional methods in cases in which the concentration of neoplastic cells is below 1%. It is expected that such a low concentration occurs frequently while patients are in remission.

Saiki et al. have recently utilized a new technique, sequence amplification by polymerase chain reaction (PCR), to diagnose sickle cell anemia prenatally (4). This technique is highly sensitive. It requires small amounts of DNA (less than 1 ug) and can amplify copies of target DNA sequences exponentially.

Recently, the present inventor has utilized polymerase chain reaction (PCR) technology to preferentially amplify the hybrid DNA sequences of a chromosomal translocation, t(14;18), characteristic of follicular lymphoma. This technique detected neoplastic cells carrying the t(14;18) in a concentration of less than 1:100,000 (5).

A major limitation of the PCR technique has been thought to involve the ability to amplify only short DNA segments (e.g., several hundred base pairs). Such amplification was feasible for the t(14;18) translocation because the molecular breakpoints on both chromosomes occurred within a limited region (6-8). However, this approach was not applicable to chromosomal translocations with more variable breakpoints, and also was not feasible for amplification of RNA without major modifications of the procedure. The present invention relates to modification of the PCR technique so that it may detect the presence of minimal amounts of aberrant gene transcripts from the neoplastic cells that carry a chromosomal translocation with variable molecular breakpoints. Neoplastic cells such as those bearing the Philadelphia Ph[1] chromosome, for example, could then be detected.

Ph[1] chromosome (t(9;22) (q34;q11)), has been observed in more than 90% of chronic myelogenous leukemia (CML) cases (9,10). Even though the breakpoints on chromosome 22q11 cluster within a small DNA segment designated as bcr (11,12), the breakpoints on chromosome 9q34 occur at variable positions up to more than 100 kilobases (kb) 5' to the second exon of the c-abl oncogene (13,14). Despite the variability of the molecular breakpoints at the DNA level, the fused bcr/abl gene in CML is transcribed into two types of chimeric mRNA: one with abl exon II linked to bcr exon "2" (designated as L-6 junction) and the other one with abl exon II linked to bcr exon "3" (designated as K-28 junction) (15). By means of RNase protection analysis, the Ph[1]-positive K562 cell line has been shown to have both types of mRNA (15). In a study of 21 Ph[1]-positive CML patients, one or both RNA junctions were detected in 19 patients (16).

SUMMARY OF THE INVENTION

The present invention involves a method for detecting the unique aberrant gene transcripts produced by a targeted cellular genomic abnormality in a tissue sample. This method comprises a series of steps. Initially, cellular RNA is extracted from the tissue sample to be analyzed for the presence of a genomic abnormality. The extracted RNA is then mixed with at least one synthetic antisense DNA oligonucleotide complementary to the unique RNA sequences of the targeted cellular genomic abnormality being detected. The mixing is under conditions facilitating formation of double stranded DNA-RNA heteroduplexes when a strand of synthetic DNA oligonucleotide is complementary to an RNA strand obtained from the tissue sample. The conditions facilitating formation are those such as time, salt concentration, temperature and pH. The synthetic DNA oligonucleotide is preferably about several hundred nucleotides in length, more preferably about 60 to about 150 nucleotides in length.

When a chromosomic abnormality characterizing residual cells of chronic myelogenous leukemia is to be detected, the preferred synthetic DNA oligonucleotide comprises anti-L6 or anti-K28 and most preferably comprises a mixture thereof. The mixture, with single stranded polynucleotides and/or oligonucleotides and DNA-RNA heteroduplexes, if any, is then treated with a single-strand specific ($S_1$) nuclease whereby single stranded RNA and single stranded DNA but not double stranded DNA-RNA heteroduplexes are hydrolyzed. A preferred nuclease is $S_1$ nuclease, Mung bean nuclease or RNase. The result of this nuclease digestion is that only DNA and RNA which were in heteroduplexes were saved from hydrolysis or digestion to nucleotides. The nuclease is next deactivated and the nuclease-resistant DNA-RNA heteroduplexes are then denatured to single stranded DNA and RNA.

The protected single stranded DNA of the denatured mixture is then subjected to at least about 20 rounds of polymerase chain reaction (PCR) to exponentially amplify targeted DNA sequences. Each round of PCR involves at least one first primer complementary to a portion of the 3' end of the antisense synthetic DNA oligonucleotide and at least one second primer identical to a portion of the 5' end of the synthetic DNA oligonucleotide. The primers are preferably oligonucleotides of between about 12 and about 20 nucleotides in length.

In a most preferred embodiment, the method of the present invention may be applied to the detection of residual cells of chronic myelogenous leukemia with its characteristic Philadelphia chromosome (Ph[1]). For this situation, the first primer is primer bcr Ex III (+) (derived from the third exon of the bcr region) or bcr Ex II (+) (derived from the second exon of the bcr region), most preferably a mixture of primer bcr Ex III (+) and bcr Ex II (+). In certain instances the second primer may also be a mixture of two different primers, particularly where there is a variable breakpoint in the second chromosomal member of the translocation characteristic of a neoplasm. Where residual cells of chronic myelogenous leukemia are being detected, the second primer is most preferably primer abl (−) derived from the second exon of the C-abl gene.

The primers are preferably kept at a concentration of about 1 micromolar (uM) in the above-described PCR reaction. This concentration is an excess for the repeated rounds of amplification. The rounds of polymerase chain reaction, when the tissue sample contained m-RNA transcripts of the targeted cellular genomic abnormality, resulted in exponential production of amplimers of unhydrolyzed antisense synthetic DNA oligonucleotide and DNA oligonucleotides complementary thereto. The presence or absence of amplimers comprising nucleotide sequences characteristic of the unique aberrant gene transcripts of the targeted cellular genomic abnormality or the complementary synthetic DNA oligonucleotide is then established. Said presence is detected only where complementary m-RNA from the tissue sample has protected the synthetic antisense DNA oligonucleotide from nuclease digestion. The method of detecting the amplimers indicative of the targeted genomic abnormality preferably involves electrophoresis of the polymerase chain reaction amplimer product and preparation of a Southern blot. In summary, the detecting step most preferably involves electrophoretic separation of amplimers, transfer to a nylon or nitrocellulose paper and exposure to a labelled oligonucleotide probe having a nucleotide sequence characteristic of the unique aberrant gene transcript of the chromosomal abnormality or a genomic component thereof.

As mentioned above, the present invention more specifically involves a method for detecting residual chronic myelogenous leukemia cells of a patient in a state of clinical remission. Said cells are characterized by the chromosomic abnormality $Ph^1$ chromosome. This more specific method comprises an analogous series of steps. The total cellular RNA or m-RNA is initially prepared from blood cells of said patient. The extracted total cellular RNA or m-RNA is then mixed with at least one synthetic DNA oligonucleotide complementary (antisense) to a characteristic portion of the aberrant gene transcripts of the $Ph^1$ chromosome. This mixing facilitates formation of double stranded DNA-RNA heteroduplexes when DNA and RNA complementary strands are present. The mixture is then treated with single-strand specific nuclease (e.g., $S_1$ nuclease) to hydrolyze single stranded RNA and single stranded DNA but not double stranded DNA-RNA heteroduplexes. The nuclease is then deactivated and the heteroduplexes denatured to form single stranded DNA and RNA.

The protected antisense DNA of the denatured mixture is then subjected to at least about 20 rounds of polymerase chain reaction with at least one first primer complementary to a portion of the 3' end of the antisense synthetic DNA oligonucleotide and at least one second primer identical to a portion of the 5' end of the antisense synthetic DNA oligonucleotide. Such a polymerase chain reaction results in the exponential production of amplimers of unhydrolyzed antisense synthetic DNA oligonucleotide and DNA oligonucleotides complementary thereto. Lastly, the presence of DNA amplimers comprising nucleotide sequences characteristic of the unique aberrant gene transcripts of the Philadelphia chromosome or the complementary synthetic DNA oligonucleotide is determined. Such presence is detected only where complementary m-RNA from the tissue sample has protected the synthetic antisense DNA oligonucleotide from nuclease digestion. The presence of these amplimers are indicative of residual cells of chronic myelogenous leukemia in the patient and may guide further therapeutic decisions.

BRIEF DESCRIPTION OF THE DRAWINGS

FIG. 1 shows the sequences of primers and synthetic antisense oligonucleotides used herein.

FIG. 2 schematically shows the combined method of the present invention.

FIG. 3 shows a Southern blot analysis of amplimers from PCR action upon DNA protected from nuclease digestion.

FIG. 3A compares PCR amplifications of anti-K28, MSL-60 (a control random base sequence DNA) and normal RNA subjected to various conditions of $S_1$ nuclease digestion. FIG. 3B shows the PCR amplification of anti-K28 and MSL-60 compared with RNA from $Ph^1$-positive CML patients.

FIG. 4 shows nuclease protection analysis of chimeric bcr/abl transcripts.

FIG. 5 shows a Southern blot analysis of genomic DNA from patient blood samples.

DESCRIPTION OF THE PREFERRED EMBODIMENT

The following examples are presented to describe preferred embodiments and utilities of the present invention and are not meant to limit the present invention unless otherwise stated in the claims appended hereto.

The present invention involves a method for detecting chromosomal abnormalities by virtue of an analysis dependent upon RNA transcripts of specific chromosomal abnormalities in question. At least one DNA oligonucleotide having a nucleotide sequence complementary to the characteristic portion of the unique aberrant gene transcripts of the chromosomal abnormality in question is synthesized. A further aspect of the present invention involves single-strand-specific nuclease-induced hydrolysis of single chain synthetic polynucleotides or oligonucleotides. The nuclease to be used is one such as $S_1$ nuclease which is unable to hydrolyze DNA-RNA heteroduplexes under the chosen conditions. The synthetic oligonucleotide is protected from hydrolysis by the nuclease when it is present as a heteroduplex with messenger RNA having a complementary nucleotide sequence. Thus, cellular extracts from, for example, a patient harboring cells with a particular chromosomal abnormality should have the characteristically transcribed messenger RNA. Extracts of the RNA would protect a complementary (antisense) synthetic oligonucleotide from nuclease digestion while oligonucleotides not protected by such heteroduplex formation would be digested to nucleotides.

In a subsequent step of the present invention, the technique of polymerase chain reaction (PCR) is applied. The PCR technique is applied, by virtue of carefully selected primers, to exponentially amplify undigested synthetic oligonucleotides. Thus, there will only be a synthetic oligonucleotide to amplify exponentially when there has been complementary messenger RNA to protect the oligonucleotide from nuclease digestion. The present invention and the method described herein are applicable to the detection of any chromosomal abnormality, particularly where that chromosomal abnormality has known transcription products.

The technique of the present invention has been specifically applied, by way of an example, to the situation found with chronic myelogenous leukemia, said leukemia being characterized by the Philadelphia chromosome. The Philadelphia chromosome (Ph[1]) in chronic myelogenous leukemia (CML) involves reciprocal translocation of the bcr gene and the c-abl oncogene. The fused bcr/abl gene is transcribed into two types of chimeric mRNA. By combining nuclease protection reaction and polymerase chain reaction technology, sequences representative of the chimeric bcr/abl transcripts were amplified exponentially. Only 5 ug of total cellular RNA was needed and the chimeric bcr/abl message could be detected at a dilution of 1:100,000 as determined by mixing studies using the RNA from the Ph[1]-positive K562 cell line. Residual chimeric bcr/abl transcripts were also detectable in remission samples from two Ph[1]-positive CML patients. This technique should allow identifications of a subpopulation of Ph[1]-positive CML patients, who, in remission, are yet at high risks of relapse.

The total cellular RNA from the K562 cell line was used to establish the feasibility of combining single-strand-specific nuclease protection and PCR to amplify sequences representative of the chimeric bcr/abl transcripts characteristic of CML. Two synthetic DNA oligonucleotides (oligomers) of 99 bases were prepared: one with a sequence antisense to the L-6 junction (anti-L6) and the other one with a sequence antisense to the K-28 junction (anti-K28), as designated in FIG. 1A (11, 15). FIG. 1 shows the sequences of the primers and synthetic antisense oligonucleotides used in practice of this embodiment of the present invention. FIG. 1(A). The sequences of the anti-K28 and anti-L6 oligomers are antisense to the K28 and the L6 mRNA junctions respectively (15). Both antisense oligomers are 99 bases in which the 50 bases on the 5' side are derived from the second exon of the abl gene and the 49 bases on the 3' side (underlined) are derived from the second exon (in case of anti-L6) or the third exon (in case of anti-K28) of the bcr region.

Also shown in FIG. 1(A) are the sequences and locations of the corresponding primers relative to the antisense oligomers: Primers bcr Ex II (+) and abl (−) for anti-L6; and Primers bcr Ex III (+) and abl (−) for anti-K28. The complementary sequences are indicated by vertical dots and the identical sequences are indicated by vertical lines. The predicted sequences amplified are 80 bp in size. FIG. 1(B) shows the sequence of the MSL-60 oligomer along with its corresponding primers [18q21(+) and $J_H$(−)] which have been described (5). Except that the 12 bases of the 3' end are complementary to the 18q21(+) primer (vertical dots) and the 12 bases of the 5' end are identical to the $J_H$(−) primer (vertical lines), the sequence of MSL-60 is randomly selected. Theoretically, it is not fully complementary to any RNA sequence.

The methods of the present invention involve use of the single-strand-specific nuclease which preferentially cleaves single stranded DNA or RNA but not the double stranded DNA-RNA heteroduplex under selected conditions (17,18). In the presence of chimeric bcr/abl transcripts, the full length antisense oligomers (either anti-L6 and/or anti-K28) would be protected from digestion upon exposure to the nuclease. In contrast, only a half length of the antisense oligomers would be protected in samples containing the bcr or abl transcripts.

FIG. 2 shows a schematic illustration of the combined method of single-strand-specific nuclease protection and PCR using the anti-K28 oligomer as an example. The anti-K28 oligomer was first allowed to hybridize with an RNA sample which contained the chimeric bcr/abl transcripts, the bcr transcript, the abl transcript and other mRNAs. The anti-K28 oligomer would be matched in full length with the chimeric bcr/abl transcript with K28 junction, but only matched in half length with the bcr transcript or the abl transcript. The single-strand-specific nuclease was then added to cleave all the single stranded and mismatched sequences. The nuclease resistant DNA-RNA heteroduplexes were then denatured and subjected to PCR by using primers bcr Ex III (+) and abl (−). In cases where only the sequence complementary to the abl region was protected, no new copies of the abl sequence (40 mer) could be synthesized because primer abl (−) had a sequence identical to the protected DNA oligomer (the right panel). In cases where the sequence complementary to the bcr region was protected, only 20 new copies of the bcr sequence (40 mer) could be made at the end of 20 cycles of PCR (the middle panel). Only when the chimeric bcr/abl transcript was present and the full length antisense oligomer was protected, new copies of sequence equivalent to the chimeric mRNA junction could be exponentially amplified (the left panel).

Following digestion of the single-strand-specific nuclease, the corresponding primers [bcr Ex II (+), bcr Ex III (+) and abl (−) (FIG. 1A)] were used and PCR performed to amplify the nuclease-resistant hybrids. The sequences could be amplified only in cases where the chimeric bcr/abl RNA transcripts were present and the full length antisense oligomers were protected (FIG. 2) from hydrolysis. The amplified sequences (amplimers) were predicted to be 80 base pairs (bp) in length (FIG. 1A). Another DNA oligomer of 60 bases with randomly selected sequence (MSL-60) and the corresponding primers [18q21(+) and $J_H$(−)] were used in the same reaction as an internal control (FIG. 1B). Since MSL-60 contained a unique sequence that would not be fully matched with any RNA sequence, it should be completely digested by the singlestrand-specific nuclease, such as $S_1$ nuclease. Amplification and detection of the 60 mers would have indicated incomplete digestion of the mismatched oligomers by nuclease.

FIG. 3 shows a Southern blot analysis of the sequences that were protected from $S_1$ nuclease digestion and amplified by PCR. The $S_1$ nuclease protection reaction contained 5 ug of total cellular RNA samples, 1 ng of anti-L6, 1 ng of anti-K28 and 1 ng of MSL-60 in 20 ul of hybridization buffer (40 mM PIPES pH 6.4, 1 mM EDTA, 0.4 M NaCl, 80% formamide). Hybridization was performed at 50° C. overnight. The samples were then diluted with 180 ul of $S_1$ nuclease reaction buffer (280 mM NaCl, 50 mM sodium acetate pH 4.6, 4.5 mM zinc sulfate) containing various units of $S_1$ nuclease and incubated at 37° C. for 1 hour. The reaction was terminated by adding 0.2 M EDTA followed by phenol/chloroform extraction. The $S_1$ nuclease resistant hybrids were then resuspended in a buffer containing 10 mM Tris pH 7.5, 50 mM NaCl, 10 mM MgCl$_2$, 1.5 mM each of dNTP, 1 uM bcr Ex II (+), 1 uM bcr Ex III (+), 1 uM abl (−), 1 uM 18q21 (+), 1 uM $J_H$(−). PCR was then performed for 25-40 cycles as described in U.S. Pat. No. 4,683,202 July 28, 1987 (Mullis) at column 17, lines 50–65 and at column 18, lines 1–5 and incorporated by reference thereto. The PCR amplified samples (5 ul) were then loaded to a 3% agarose minigel and subjected to electrophoresis (50 V) for 4 hours. The gel was then denatured, neutralized and transferred to a nylon filter. The filter was prehybridized as described (4) and then hybridized with a mixture of $^{32}$P-labelled anti-K26, anti-L6, MSL-60 (specific activity > 5 uCi/pmol) at 42° C. for 18 hours. The washing condition and autoradiography were carried out as described (4).

FIG. 3(A) shows PCR amplification of 25 pg of anti-K28 (Lane 1) and MSL-60 (Lane 2) without prior $S_1$ nuclease treatment for 10 cycles. The amplified segments were approximately 80 bp (Lane 1) and 60 bp (Lane 2) as predicted. Lanes 3 and 4: the normal RNA inadequately treated with $S_1$ nuclease and then PCR amplified for 20 and 25 cycles respectively. Two bands that were 80 bp and 60 bp in size were detected in both lanes, indicating false positivity. Lanes 5 and 7: the normal RNA treated with increasing concentrations of $S_1$ nuclease and then PCR amplified for 25 cycles. Neither the 80 bp band nor the 60 bp band was detected. The faint shadow in Lane 7 appeared to be a background shadow in our original autoradiograph. Lanes 6 and 8: the RNA samples from the K562 cell line treated with $S_1$ nuclease and PCR amplified for 25 cycles. The concentrations of $S_1$ nuclease used in Lanes 6 and 8 were the same as those used in Lanes 5 and 7 respectively. In both instances, the 80 bp band representative of the chimeric bcr/abl transcripts was clearly demonstrated and the "internal control" 60 mer was absent.

FIG. 3(B) shows 25 pg of anti-K28 (Lane 1) and MSL-60 (Lane 2) without prior $S_1$ nuclease treatment PCR amplified for 15 cycles. Lanes 3 and 4: a sample containing 0.05 ng of total RNA from the K562 cell line and 5 ug of the normal RNA subjected to $S_1$ nuclease digestion followed by PCR amplification for 32 and 40 cycles respectively. A strong and convincing band of 80 bp was detected in both lanes. Lanes 5 (patient A) and 6 (patient B): the total RNAs of the remission blood samples obtained from two Ph$^1$-positive CML patients treated with $S_1$ nuclease and PCR amplified for 35 cycles. A band of 80 bp representative of the chimeric bcr/abl transcripts was clearly demonstrated in both. The molecular weight markers were labelled on the left side of the figures.

As shown in FIG. 3A, lanes 3 and 4, both the 80 mers and 60 mers were amplified in the RNA sample from a normal lymph node (referred to hereafter as normal RNA), that was inadequately treated with $S_1$ nuclease. When adequate amounts of $S_1$ nuclease were added to the normal RNA samples, neither the antisense oligomers nor the "internal control" oligomer was protected. These unprotected oligomers were not amplified (FIG. 3A, Lanes 5 and 7). In contrast, only the antisense oligomers were protected by RNA samples of the K562 cell line when adequately treated with $S_1$ nuclease and subsequently amplified (FIG. 3A, Lanes 6 and 8).

To determine the sensitivity of this combined nuclease-protection and PCR technique in comparison with a $S_1$ nuclease protection assay alone, a mixing experiment was performed. FIG. 4 shows $S_1$ nuclease protection analysis of the chimeric bcr/abl transcripts in the K562 cell line and two Ph$^1$-positive CML patients. Samples (25 ug) of total cellular RNA were coprecipitated with $^{32}$P-labelled anti-K28, anti-L6, and MSL-60 (10$^6$ cpm each), then resuspended in hybridization buffer, incubated at 50° C. overnight and treated with $S_1$ nuclease as described in the legend of FIG. 3. The $S_1$ nuclease resistant hybrids were precipitated and subjected to electrophoresis in 8% polyacrylamide gel. The gel was then dried and autoradiographed. Lane 1: end-labelled molecular weight markers ($\phi \times 174$, Hae III). Lane 2: the normal RNA treated with $S_1$ nuclease (Bethesda Research Laboratory, Gaithersburg, Md.) at the concentration of 5 units/ul. Incompletely digested 99 mers and 60 mers (arrow heads) were detected. The $S_1$ nuclease used in Lanes 3–10 was at 20 units/ul. Lane 3: the normal RNA in which no $S_1$ nuclease resistant hybrids were detected. Lane 4: the total RNA sample (25 ug) from the K562 cell lines. A strong band of 99 bases in size was demonstrated (arrow). Since the 60 mer was not detected, the 99 bp band should represent antisense oligomer that was protected by the chimeric bcr/abl transcripts. Multiple faint bands detected in this assay were due to partial exonuclease cleavage on the DNA-RNA duplex by $S_1$ nuclease. Lane 5: 2.5 ug of the K562 RNA in 22.5 ug of the normal RNA. A very faint band of 99 bp in size was barely detected (arrow). Lane 6: 0.25 ug of the K562 RNA in 25 ug of the normal RNA. No band was detectable. Lanes 7 and 8: the pretreatment (Lane 7) and remission (Lane 8) blood samples obtained from Patient A. Lanes 9 and 10: the pretreatment (Lane 9) and remission (Lane 10) blood samples obtained from Patient B. No $S_1$ nuclease resistant hybrids were detected in Lanes 7–10. By means of a $S_1$ nuclease protection assay using radiolabelled anti-K28, anti-L6 and MSL-60, the presence of the chimeric bcr/abl transcripts could be detected in a sample containing 25 ug of total RNA from the K562 cell line (FIG. 4, Lane 4). In samples with further dilutions, a faint and questionable band could barely be detected in the sample containing 2.5 ug of total RNA from the K562 cell line and 22.5 ug of the normal RNA (FIG. 4, Lane 5). In contrast, a strong and convincing band representative of the chimeric bcr/abl transcripts could be detected in a sample containing 0.05 ng of total RNA from the K562 cell line and 5 ug of the normal RNA (i.e 1:100,000 dilution) by the present method combining $S_1$ nuclease protection and PCR (FIG. 3B, Lanes 3 and 4).

Sequential follow up studies were also performed in blood samples obtained from two CML patients who had achieved complete hematologic remission resulting from recombinant alpha interferon therapy. FIG. 5 shows Southern blot analysis of the genomic DNAs from the blood samples of patients A and B. High molecular weight DNAs were digested with restriction endonuclease-BglII, fractionated in a 0.8% agarose gel and transferred onto a nylon filter, which was then hybridized with a 1.2 kb HindIII-BglII bcr probe (Oncogene Science Inc.). Lane 1: genomic DNA from the normal lymph node. Lanes 2 and 3: the pretreatment (Lane 2) and remission (Lane 3) blood samples obtained from patient A. Lane 4 and 5: the pretreatment (Lane 4) and remission (Lane 5) blood samples obtained from patient B.

While these two patients were in the chronic phase of disease, the blood samples obtained were shown to have Ph$^1$ chromosome by karyotyping and clonal bcr gene rearrangement by Southern blot analysis (FIG. 5, Lanes 2 and 4). The chimeric bcr/abl transcripts of these patients were too low in abundance to be detected by using 25 ug of total cellular RNA and $S_1$ nuclease protection analysis (FIG. 4, Lanes 7 and 9). At the time of remission, karyotyping showed 100% diploid cells, Southern blot analysis showed no bcr gene rearrangement (FIG. 5, Lanes 3 and 5) and $S_1$ nuclease protection assay showed no chimeric bcr/abl transcripts (FIG. 4, Lanes 8 and 10). However, residual chimeric bcr/abl transcripts were detected in both remission samples by the modified PCR technique of the present invention (FIG. 3B, Lanes 5 and 6).

Modified PCR technique of the present invention is a novel approach for the detection of minimal residual disease in $Ph^1$-positive CML. This technique provides the opportunity to detect minimal amounts of aberrant gene products from neoplastic cells that carry a chromosomal translocation. Since it detects minimal numbers of $Ph^1$-positive cells that are not detectable by other modalities, it may be used to identify a subpopulation of $Ph^1$-positive CML patients in remission, who are at high risk of relapse. Since it requires only 5 ug of total cellular RNA samples, it represents a simple and practical method for clinical usage. It will also be helpful in understanding the clinical and biological significance of minimal residual disease in $Ph^1$-positive CML. Accordingly, such information may be used to design new therapeutic strategies for neoplastic disease.

The following cited references are incorporated by reference herein for the observations and methods for which they were earlier cited.

REFERENCES CITED

1. A. Hagenbeck, B. Lowerberg, Minimal Residual Disease in Acute Leukemia (Martinus Nijhoff Press, 1986).
2. E. Hu et al., Lancet II, 1092 (1985).
3. M. L. Cleary, J. Chao, R. Warnke, J. Sklar, Proc. Natl. Acad. (USA), 81:593 (1984).
4. R. K. Saiki, et al., Science, 230:1350 (1985).
5. M. S. Lee et al., ibid., 237:175 (1987).
6. Y. Tsujimoto et al., ibid, 228:1440 (1985).
7. M. L. Cleary, S. D. Smith, J. Sklar, Cell, 47:19 (1986).
8. A. Bakhshi et al., Proc. Natl. Acad. Sci. (USA), 84:2396 (1987).
9. J. D. Rowley, Nature, 243:299 (1983).
10. J. Whang-Peng et al., Blood, 32:755 (1968).
11. J. Groffen et al., Cell, 36:93 (1984).
12. N. Heisterkamp et al., Nature, 315:758 (1985).
13. N. Heisterkamp et al., Nature, 306:239 (1983).
14. A. Bernards et al., Mol. Cell. Biol., 7:3231 (1987).
15. E. Shtivelman et al., Cell, 48:277 (1986).
16. E. Shtivelman et al., Blood, 69:971 (1986).
17. A. J. Berk, P. A. Sharp, Cell, 12:721 (1977).
18. T. Ando, Biochem. Biophys. Acta, 114:158 (1966).

Changes may be made in the operation and arrangement of the various steps and procedures described herein without departing from the concept and scope of the invention as defined in the following claims.

What is claimed is:

1. A method for detecting the unique aberrant gene transcripts of a targeted cellular genomic abnormality in a tissue sample, the method comprising the steps of:
   preparing m-RNA or total cellular RNA from the tissue sample;
   mixing the m-RNA or total cellular RNA with at least one antisense synthetic DNA oligonucleotide complementary to the unique RNA sequence of the targeted cellular genomic abnormality, said mixing facilitating formation of double stranded DNA-RNA heteroduplexes when DNA and RNA complementary strands are present;
   adding a control DNA oligomer characterized as having a base sequence and size different from that of the antisense synthetic DNA oligonucleotide;
   treating the mixture with a single strand-specific nuclease whereby single stranded RNA and single stranded DNA but not double stranded DNA-RNA heteroduplexes are hydrolyzed;
   deactivating the nuclease and denaturing unhydrolyzed heteroduplexes to form a mixture of single stranded DNA and RNA;
   subjecting the single stranded DNA of the denatured mixture to at least about 20 rounds of polymerase chain reaction with at least one first primer complementary to a portion of the 3' end of the antisense synthetic DNA oligonucleotide, at least one second primer identical to a portion of the 5' end of the antisense synthetic DNA oligonucleotide, and at least two control primers, a first control primer being complementary to at least a portion of one end of the 3' end and a second control primer being complementary to at least a portion of the 5' end of the control DNA oligomer, said polymerase chain reaction resulting in amplimers of unhydrolyzed synthetic DNA oligonucleotide and DNA oligonucleotides complementary thereto; and
   detecting the presence of amplimers comprising nucleotide sequences characteristic of the unique aberrant gene transcripts of the targeted cellular genomic abnormality or the complementary synthetic DNA oligonucleotide, said presence being detected only where complementary m-RNA from the tissue sample has protected the synthetic antisense DNA oligonucleotide from nuclease digestion and wherein detection of amplimers is quantitatively related to aberrant gene transcripts, provided that amplified control DNA oligomer is absent, as an indication of complete single-strand nuclease hydrolysis.

2. A method for detecting residual chronic myelogenous leukemia cells of a patient in a state of clinical remission, said cells being characterized as having the $Ph^1$ chromosome capable of producing unique genomic transcripts, the method comprising the steps of:
   preparing the total cellular RNA or m-RNA from blood cells of said patient;
   mixing the total cellular RNA or m-RNA with a synthetic antisense DNA oligonucleotide complementary to characteristic RNA sequences of the $Ph^1$ chromosome, said mixing facilitating formation of double stranded DNA-RNA heteroduplexes when DNA and RNA complementary strands are present;
   adding a control DNA oligomer characterized as having a base sequence and size different from that of the antisense synthetic DNA oligonucleotide;
   treating the mixture with a single-strand-specific nuclease to hydrolyze single stranded RNA and single stranded DNA but not double stranded DNA-RNA heteroduplexes;
   deactivating the nuclease and denaturing unhydrolyzed heteroduplexes to form a mixture of single stranded DNA and RNA;
   subjecting the single stranded DNA of the denatured mixture to at lest about 20 rounds of polymerase chain reaction with at least one first primer complementary to a portion of the 3' end of the antisense synthetic DNA oligonucleotide and a second primer identical to a portion of the 5' end of the antisense synthetic DNA oligonucleotide, and at least two control primers, a first control primer being complementary to at least a portion of the 3' end and a second control primer being complementary to at least a portion of the 5' end of the control DNA oligomer, said polymerase chain reaction resulting in amplimers of unhydrolyzed synthetic DNA oligonucleotide and DNA oligonucleotides complementary thereto; and detecting the presence of amplimers comprising nucleotide sequences characteristic of unique gene transcripts of the Philadelphia chromosome or the complementary synthetic DNA oligonucleotide, said presence being detected only where complementary m-RNA from the tissue sample has protected the synthetic DNA oligonucleotide from nuclease digestion and wherein the presence of amplimers is quantitatively related to the unique genomic transcripts derived from the $Ph^1$ chromosome provided that amplimers generated from the added control DNA oligomer are absent, as an indication of complete single-strand nuclease hydrolysis.

3. The method of claim 1 or 2 wherein the primers are oligonucleotides of between about 12 and about 20 nucleotides in length.

4. The method of claim 1 or 2 wherein the primers are oligonucleotides of about 12 nucleotides in length.

5. The method of claim 1 or 2 wherein the first primer is primer bcr Ex III (+) derived from the third exon of the bcr region or bcr Ex II (+) derived from the second exon of the bcr region.

6. The method of claim 1 or 2 wherein the first primer is defined further as being a mixture of primer bcr Ex III (+) and primer bcr Ex II (+).

7. The method of claim 1 or 2 wherein the first primer is defined further as being a mixture of two different primers.

8. The method of claim 1 wherein the second primer is defined further as being a mixture of two different primers.

9. The method of claim 1 or 2 wherein the second primer is primer abl (−) derived from the second exon of the abl gene.

10. The method of claim 1 or 2 wherein the primers are at a concentration of about 1 uM.

11. The method of claim 1 or 2 wherein the synthetic antisense DNA oligonucleotide is from about 60 to about 150 nucleotides in length.

12. The method of claim 1 or 2 wherein the synthetic antisense DNA oligonucleotide is about several hundred bases in length.

13. The method of claim 1 or 2 wherein the synthetic DNA oligonucleotide comprises sequence antisense to the L6 mRNA junction (anti-L6).

14. The method of claim 1 or 2 wherein the synthetic DNA oligonucleotide comprises sequence antisense to K-28 m-RNA junction (anti-K28).

15. The method of claim 1 or 2 wherein the synthetic DNA oligonucleotide comprises anti-L6 and anti-K28.

16. The method of claim 1 wherein the targeted cellular genomic abnormality is the Philadelphia chromosome, $Ph^1$.

17. The method of claim 1 wherein the nuclease is single-strand-specific nuclease, such as $S_1$ nuclease, Mung bean nuclease or RNase.

18. The method of claim 1 or 2 wherein the detecting step involves electrophoresis of the polymerase chain reaction amplimer product.

19. The method of claim 1 or 2 wherein the detecting step involves preparation of a Southern blot.

20. The method of claim 1 or 2 wherein the detecting step involves electrophoretic separation of amplimers, transfer to a nylon or nitrocellulose paper and exposure to a labelled oligonucleotide probe having a nucleotide sequence characteristic of the unique aberrant gene transcripts of the chromosomal abnormality or a genomic component thereof.

21. The method of claim 1 or claim 2 wherein the control DNA oligomer, except for 12 bases on each of its ends, is a randomly selected 60-base DNA oligomer essentially lacking complementarity with the mRNA derived from genes associated with aberrant gene transcripts.

22. The method of claim 2 wherein the genomic transcripts are chimeric bcr/abl transcripts.

23. The method of claim 1 or claim 2 wherein one control DNA primer is 18q21(+) complementary to 12 bases of the 3' end and the other control DNA primer is $J_H(-)$ identical to 12 bases at the 5' end of the control DNA oligomer.

24. The method of claim 2 wherein one antisense synthetic DNA oligonucleotide comprises 99 bases having a sequence antisense to junction K28 and the other antisense synthetic DNA oligonucleotide comprises 99 bases having a sequence antisense to junction L6 of the chimeric transcripts characteristic of chronic myelogenous leukemia.

25. The method of claim 24 wherein both antisense oligonucleotides include 50 bases from an abl gene second exon and 49 bases from a bcr gene second or third exon, wherein the 50 bases are associated with a 5' end and the 49 bases with a 3' end.

26. The method of claim 1 or 2 wherein the primers for the antisense synthetic DNA nucleotide are identical to the primers for the control DNA oligomer.

27. The method of claim 1 or 2 wherein the first primer and the second primer are between about 12 and about 20 nucleotides in length.

* * * * *